United States Patent [19]

Behler et al.

[11] Patent Number: 5,489,395

[45] Date of Patent: Feb. 6, 1996

[54] DETERGENT COMPOSITIONS

[75] Inventors: Ansgar Behler, Bottrop; Brigitte Giesen, Duesseldorf; Hans-Christian Raths, Monheim, all of Germany; Harald P. Wulff, Bryn Mawr, Pa.

[73] Assignee: Henkel Kommanditgesellschaft auf Aktien, Duesseldorf, Germany

[21] Appl. No.: 315,664

[22] Filed: Sep. 30, 1994

Related U.S. Application Data

[63] Continuation of Ser. No. 116,658, Sep. 2, 1993, abandoned.

[51] Int. Cl.$^6$ ............................. C11D 1/18; C11D 1/38; C11D 1/12; C11D 1/755

[52] U.S. Cl. ............................. 252/174.17; 252/174.21; 252/545; 252/550; 252/551

[58] Field of Search ..................... 252/174.17, 174.21, 252/545, 550, 551

[56] References Cited

U.S. PATENT DOCUMENTS

| | | | |
|---|---|---|---|
| 4,116,986 | 9/1978 | Bistline, Jr. et al. | 260/401 |
| 4,331,447 | 5/1982 | Kamada et al. | 44/20 |
| 4,483,780 | 11/1984 | Llenado | 252/174.17 |
| 4,599,188 | 6/1986 | Llenado | 252/174.17 |
| 5,025,069 | 6/1991 | Deguchi et al. | 252/552 |
| 5,034,555 | 7/1991 | O'Lenick, Jr. | 558/30 |
| 5,043,091 | 8/1991 | Joshi et al. | 252/174.17 |
| 5,205,959 | 4/1993 | Schmid et al. | 252/174 |
| 5,242,615 | 9/1993 | Urfer et al. | 252/174.25 |
| 5,258,358 | 11/1993 | Kocur et al. | 504/205 |

FOREIGN PATENT DOCUMENTS

| | | | |
|---|---|---|---|
| 0075996 | 4/1983 | European Pat. Off. | C11D 3/22 |
| 0070075 | 1/1987 | European Pat. Off. | C11D 1/83 |
| 0070074 | 1/1987 | European Pat. Off. | C11D 1/83 |
| 0070077 | 1/1987 | European Pat. Off. | C11D 1/86 |
| 0070076 | 1/1987 | European Pat. Off. | C11D 1/86 |
| 0075995 | 5/1987 | European Pat. Off. | C11D 3/22 |
| 0301298 | 2/1989 | European Pat. Off. | C07H 15/04 |
| 3843713 | 11/1989 | Germany | C07B 41/04 |
| 4010606 | 10/1991 | Germany | B01J 31/04 |
| 8809369 | 12/1988 | WIPO | C11D 17/00 |
| 9003977 | 9/1989 | WIPO | C07H 15/04 |
| 9105764 | 10/1990 | WIPO | C07C 305/10 |
| 9103538 | 3/1991 | WIPO | C11D 1/825 |
| 9209569 | 6/1992 | WIPO | C07C 305/10 |
| 9209570 | 6/1992 | WIPO | C07C 305/10 |

OTHER PUBLICATIONS

Tenside Surf. Det. 28, 1991, pp. 413–418.
Fat Sci. Technol. 92, 1990, pp. 109–114.
J. Am. Oil Chem. Soc. 63, 1986, p. 691.
Happi, 1986, p. 52.
J. Am. Oil Chem. Soc., 68, pp. 629–634 Aug. 1991.
Fette, Seifen, Anstrichmitt, 74, 1972, p. 163.
DIN 53-902, 1981, pp. 1–3.
Kosmetische Färbemittel, Weinheim, 1984, pp. 81–106.

*Primary Examiner*—Paul Lieberman
*Assistant Examiner*—Patricia L. Hailey
*Attorney, Agent, or Firm*—Wayne C. Jaeschke; John E. Drach; Henry E. Millson, Jr.

[57] ABSTRACT

Water containing detergent mixtures contain an alkyl and/or alkenyl polyglycoside and an anionic or nonionic surfactant selected from the group consisting of: (a) a narrow range fatty alcohol polyglycol ether, (b) a narrow range fatty alcohol ether sulfate, (c) a fatty acid alkanolamide ether sulfate, and (d) a monoglyceryl ether sulfate are superior detergents for dishwashing formulations and for cosmetics.

5 Claims, No Drawings

DETERGENT COMPOSITIONS

This application is a continuation of application Ser. No. 08/116,658 filed on Sep. 2, 1993, abandoned.

BACKGROUND OF THE INVENTION

1. Field of the Invention

This invention relates to water containing detergent mixtures comprising alkyl and/or alkenyl oligoglycosides and other selected anionic and nonionic surfactants, to surface active preparations containing these mixtures and to the use of the mixtures for the production of the surface active preparations.

2. Description of the Related Art

Alkyl oligoglycosides and, in particular, alkyl oligoglucosides are nonionic surfactants which, by virtue of their native raw material base (fatty alcohol and sugar), are acquiring increasing significance and are used, for example, in manual dishwashing detergents or cosmetic products. However, despite good performance results, there is still a need for detergent mixtures based on alkyl glucosides of which the performance level synergistically exceeds that of the individual components.

There has hitherto been no shortage of attempts to develop detergent mixtures based on alkyl oligoglucosides which have advantageous properties.

However, where these detergent mixtures are used in surface active preparations, reductions in performance and ecotoxicological compatibility was observed.

SUMMARY OF THE INVENTION

The present invention relates to water containing detergent mixtures comprising an alkyl and/or alkenyl oligoglycoside and an anionic or nonionic surfactant selected from the group consisting of: (a) a narrow range fatty alcohol polyglycol ether, (b) a narrow range fatty alcohol ether sulfate, (c) a fatty acid alkanolamide ether sulfate, and (d) a monoglyceryl ether sulfate.

It has surprisingly been found that the detergent compositions according to the invention have a washing, dishwashing, foaming and cleaning power and a skin-cosmetic compatibility which exceed those of the individual components through synergistic enhancement.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

The alkyl polyglucosides which can be used in the compositions according to the invention have the formula I

$$R^1O(G)_n \qquad (I)$$

wherein $R^1$ is an alkyl or alkenyl group containing from about one to about 30 carbon atoms; G represents a moiety derived from a reducing saccharide containing from 5 or 6 atoms; n is a number having an average value from 1 to about 6. Such alkyl polyglycosides are commercially available as APG®, Glucopon™, or Plantaren™ surfactants from Henkel Corporation, Ambler, Pa., 19002. Examples of such surfactants include but are not limited to:

1. APG® 225—an alkylpolyglycoside in which the alkyl group contains 8 to 10 carbon atoms.
2. APG® 425—an alkyl polyglycoside in which the alkyl group contains 8 to 16 carbon atoms.
3. APG® 625—an alkyl polyglycoside in which the alkyl groups contains 12 to 16 carbon atoms.
4. APG® 300—an alkyl polyglycoside substantially the same as the 325 product above but having a different average degree of polymerization.
5. Glucopon™ 600—an alkylpolyglycoside substantially the same as the 625 product above but having a different average degree of polymerization.
6. Plantaren™ 2000—a $C_{8-16}$ alkyl polyglycoside having an average degree of polymerization of 1.4.
7. Plantaren™ 1300—a $C_{12-16}$ alkyl polyglycoside having an average degree of polymerization of 1.6.
8. Plantaren™ 1200—a $C_{12-16}$ alkyl polyglycoside having an average degree of polymerization of 1.4. Other examples include alkyl polyglycoside surfactant compositions which are comprised of mixtures of compounds of formula I wherein G represents a moiety derived from a reducing saccharide containing 5 or 6 carbon atoms; n is a number from 1.8 to 3; and $R^1$ is an alkyl radical having from 8 to 20 carbon atoms. The composition is characterized in that it has increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglucosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in copending application Ser. No. 07/810,588, filed on 12/19/91, the entire contents of which are incorporated herein by reference. Alkyl and/or alkenyl oligoglycosides having a degree of oligomerization below 1.7 and, more particularly, between 1.2 and 1.4 are preferred from the performance point of view. Particularly preferred alkyl polyglycosides include those having a DP of from 1 to 3 and in which the alkyl group is derived from technical $C_{9-11}$ oxoalcohols and/or hydrogenated $C_{12-14}$ coconut oil alcohols.

The narrow range fatty alcohol polyglycol ethers suitable for use in accordance with the invention correspond to formula (II)

$$R^2\text{—}O\text{—}(CH_2CH_2O)_nH \qquad (II)$$

wherein $R^2$ is a linear or branched alkyl or alkenyl radical containing 6 to 22 carbon atoms and n is a number of 1 to 10. These substances are also known chemical compounds which may be obtained, for example, by ethoxylation of fatty alcohols or oxoalcohols in the presence of selected homogeneous catalysts, such as for example alkaline earth metal salts of alkoxyhydroxy fatty acids or ether carboxylic acids as taught by Fat. Sci. Technol. 92, 109 (1990), or heterogeneous systems such as, for example, calcined hydrotalcite as taught in DE-A-38 43 713 or hydrophobicized hydrotalcite as taught in DE-A-40 10 606. These products, which are also known as narrow-range ethoxylates (NRE), are distinguished from conventional fatty alcohol polyglycol ethers by a comparatively lower content of homologs with relatively low and relatively high degrees of ethoxylation and by a distinctly reduced content of free residual alcohol. A more detailed description of this class of compounds can be found, for example, in J. Am. Oil Chem. Soc. 63, 691 (1986) and HAPPI, 52 (1986). Detergent mixtures having particularly good performance properties, more particularly a high basic foam and ready thickenability, are obtained using fatty alcohol polyglycol ethers which have been produced in the presence of calcined or, in particular, hydrophobicized hydrotalcite and which show a particularly advantageous narrowing of the homolog distribution. Compounds of formula (II), in which $R^2$ is a $C_{12-18}$ and, more particularly, $C_{12-14}$ alkyl radical and n is a number of 2 to 7, are also preferred.

The narrow range fatty alcohol ether sulfates which may be used in accordance with the invention correspond to formula (III)

$$R^3-O-(CH_2CH_2O)_n-SO_3X \qquad (III)$$

wherein $R^3$ is a linear or branched alkyl or alkenyl radical containing 6 to 22 carbon atoms, n is a number of 1 to 10 and X is an alkali metal or alkaline earth metal. These substances are also known chemical compounds which may be obtained by sulfation of the above-mentioned narrow-range fatty alcohol polyglycol ethers. Preparative and performance particulars are disclosed in International patent application WO 91/05 764 and in J. Am. Oil Chem. Soc. 68, 629 (1991). Typical examples are the sulfation products of adducts of 1 to 10 mol ethylene oxide (narrow-range) with 1 mol caproic alcohol, capryl alcohol, capric alcohol, lauryl alcohol, myristyl alcohol, cetyl alcohol, palmitoleyl alcohol, stearyl alcohol, oleyl alcohol, elaidyl alcohol, petroselinyl alcohol, arachyl alcohol, gadoleyl alcohol, behenyl alcohol and erucyl alcohol and technical mixtures thereof. Narrow-range sulfates of adducts of 2 to 7 mol ethylene oxide with saturated coconut oil fatty alcohols in the form of their sodium or potassium salts are preferred. Fatty alcohol ether sulfates derived from corresponding fatty alcohol polyglycol ethers which, in turn, have been produced in the presence of calcined or, more particularly, hydrophobicized hydrotalcite and which therefore show a particularly advantageous narrow homolog distribution, are preferably used.

The fatty acid alkanolamide ether sulfates which may be used in accordance with the invention correspond to formula (IV)

$$R^4CO-N-[Z]-O(CH_2CH_2O)_p-SO_3X \qquad (IV)$$
$$\phantom{R^4CO-N}\underset{R^5}{|}$$

wherein $R^4CO$ is a linear or branched acyl radical containing 6 to 22 carbon atoms, [Z] is an ethylene, n-propylene or i-propylene group, $R^5$ is hydrogen or a $Z-O(CH_2-CH_2O)_p-SO_3X$ group, p is 0 or a number of 1 to 20 and X is an alkali metal or alkaline earth metal. These substances are also known compounds which may be obtained, for example, by sulfation of fatty acid alkanolamides or ethoxylation products thereof and subsequent neutralization as taught in U.S. Pat. Nos. 4,116,986, 5,034,555. Typical examples are the reaction products of lauric acid monoethanolamide, lauric acid diethanolamide, coconut oil fatty acid monoethanolamide, coconut oil fatty acid monopropanolamide, coconut oil fatty acid diethanolamide, coconut oil fatty acid dipropanolamide, coconut oil fatty acid di-i-propanolamide, stearic acid monoethanolamide, tallow fatty acid monoethanolamide and tallow fatty acid diethanolamide and also ethylene oxide adducts thereof with sulfur trioxide or chlorosulfonic acid in the form of their sodium salts. Fatty acid alkanolamide sulfates corresponding to formula (IV), in which $R^4CO$ is a $C_{12-18}$ acyl radical $R^5$ is hydrogen, [Z] is an ethylene group and p= 0, are preferably used.

The monoglyceride (ether) sulfates suitable for use in accordance with the invention correspond to formula (V)

$$\begin{array}{l} CH_2O(CH_2CH_2O)_x-COR^6 \\ | \\ CH-O(CH_2CH_2O)_y-H \\ | \\ CH_2O(CH_2CH_2O)_z-SO_3X \end{array} \qquad (V)$$

wherein $R^6CO$ is a linear or branched acyl radical containing 6 to 22 carbon atoms, x, y and z together have a value of 0 or 1 to 30 and X is an alkali metal or alkaline earth metal. These substances are also known chemical compounds which may be obtained, for example, by sulfation of partial glycerides or ethylene oxide adducts thereof and subsequent neutralization as disclosed in WO 92/09 569 and WO 92/09 570. Typical examples are the reaction products of lauric acid monoglyceride, coconut oil fatty acid monoglyceride, palmitic acid monoglyceride, stearic acid monoglyceride, oleic acid monoglyceride and tallow fatty acid monoglyceride and ethylene oxide adducts thereof with sulfur trioxide or chlorosulfonic acid in the form of their sodium salts. Monoglyceride sulfates corresponding to formula (V), in which $R^6CO$ is a linear acyl radical containing 8 to 18 carbon atoms, are preferably used.

The water-containing detergent mixtures according to the invention may contain the alkyl and/or alkenyl oligoglycosides in quantities of 1 to 99% by weight and preferably 30 to 75% by weight, based on the solids content of the mixtures. The other constituents, which form groups b), may make up from 1 to 75% by weight, preferably 10 to 70% by weight and, more preferably, 25 to 60% by weight of the detergent mixtures.

The water-containing detergent mixtures may be produced by simple mechanical mixing of aqueous solutions of the components, optionally at elevated temperatures of 30° to 50° C.; no chemical reaction takes place during the mixing process.

The compositions according to the invention can be useful in the following types of products: (a) powder form universal detergents containing 10 to 30% by weight, based on the detergent, of a mixture of alkyl and/or alkenyl oligoglycosides and other anionic and/or nonionic surfactants selected from the group consisting of narrow-range fatty alcohol polyglycol ethers, narrow-range fatty alcohol ether sulfates, fatty acid alkanolamide (ether) sulfates and monoglyceride (ether) sulfates and, optionally, other typical auxiliaries and additives; (b) liquid universal detergents containing 10 to 70% by weight, based on the detergent, of a mixture of alkyl and/or alkenyl oligoglycosides and other anionic and/or nonionic surfactants selected from the group consisting of narrow-range fatty alcohol polyglycol ethers, narrow-range fatty alcohol ether sulfates, fatty acid alkanolamide (ether)

sulfates and monoglyceride (ether) sulfates and, optionally, other typical auxiliaries and additives; (c) liquid light-duty detergents containing 10 to 50% by weight, based on the detergent, of a mixture of alkyl and/or alkenyl oligoglycosides and other anionic and/or nonionic surfactants selected from the group consisting of narrow-range fatty alcohol polyglycol ethers, narrow-range fatty alcohol ether sulfates, fatty acid alkanolamide (ether) sulfates and monoglyceride (ether) sulfates and, optionally, other typical auxiliaries and additives; (d) liquid cleaning and disinfecting preparations containing 10 to 30% by weight, based on the preparation, of a mixture of alkyl and/or alkenyl oligoglycosides and other anionic and/or nonionic surfactants selected from the group consisting of narrow-range fatty alcohol polyglycol ethers, narrow-range fatty alcohol ether sulfates, fatty acid alkanolamide (ether) sulfates and monoglyceride (ether) sulfates and, optionally, other typical auxiliaries and additives; (e) hair shampoos containing 10 to 30% by weight, based on the shampoo, of a mixture of alkyl and/or alkenyl oligoglycosides and other anionic and/or nonionic surfactants selected from the group consisting of narrow-range fatty alcohol polyglycol ethers, narrow-range fatty alcohol ether sulfates, fatty acid alkanolamide (ether) sulfates and monoglyceride (ether) sulfates and, optionally, other typical auxiliaries and additives; (f) hair rinses containing 10 to 30% by weight, based on the hair rinse, of a mixture of alkyl and/or alkenyl oligoglycosides and other anionic and/or nonionic surfactants selected from the group consisting of narrow-range fatty alcohol polyglycol ethers, narrow-range fatty alcohol ether sulfates, fatty acid alkanolamide (ether) sulfates and monoglyceride (ether) sulfates and, optionally, other typical auxiliaries and additives; (g) foam baths containing 10 to 30% by weight, based on the foam bath, of a mixture of alkyl and/or alkenyl oligoglycosides and other anionic and/or nonionic surfactants selected from the group consisting of narrow-range fatty alcohol polyglycol ethers, narrow-range fatty alcohol ether sulfates, fatty acid alkanolamide (ether) sulfates and monoglyceride (ether) sulfates and, optionally, other typical auxiliaries and additives.

Detergents based on the detergent mixture according to the invention may contain, for example, builders, salts, bleaches, bleach activators, optical brighteners, redeposition inhibitors, solubilizers, foam inhibitors and enzymes as auxiliaries and additives.

Typical builders are sodium aluminium silicates (zeolites), phosphates, phosphonates, ethylenediamine tetraacetic acid, nitrilotriacetate, citric acid and/or polycarboxylates. Suitable salts or diluents are, for example, sodium sulfate, sodium carbonate or sodium silicate (waterglass). Typical individual examples of other additives are sodium borate, starch, sucrose, polydextrose, TAED, stilbene compounds, methyl cellulose, toluene sulfonate, cumene sulfonate, long-chain soaps, silicones, mixed ethers, lipases and proteases.

Hair shampoos, hair lotions or foam baths based on the detergent mixtures according to the invention may contain, for example, emulsifiers, oil components, fats and waxes, thickeners, superfatting agents, biogenic agents, film formers, fragrances, dyes, pearlescers, preservatives and pH regulators as auxiliaries and additives.

Typical components are such substances as paraffin oil, vegetable oils, fatty acid esters, squalene and 2-octyl dodecanol. Suitable fats and waxes are, for example, spermaceti, beeswax, montan wax, paraffin and cetostearyl alcohol. Superfatting agents may be selected from such substances as, for example, polyethoxylated lanolin derivatives, lecithin derivatives and fatty acid alkanolamides, the fatty acid alkanolamides also serving as foam stabilizers. Suitable thickeners are, for example, polysaccharides, more particularly xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone and electrolytes, such as sodium chloride and ammonium chloride. Biogenic agents are understood to be, for example, vegetable extracts, protein hydrolyzates and vitamin complexes. Typical film formers are, for example, polyvinyl pyrrolidone, vinyl pyrrolidine/vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlescers are, for example, glycol distearic acid esters, such as ethylene glycol distearate, and also fatty acid monoglycol esters. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984. These dyes are typically used in concentrations of 0.001 to 0.1% by weight, based on the mixture as a whole.

The compositions according to the invention can also be used in the production of laundry detergents, dishwashing detergents and cleaning preparations, hair-care and personal hygiene preparations, in which they may be present in quantities of 1 to 50% by weight and preferably in quantities of 10 to 30% by weight, based on the preparation.

The following Examples are intended to illustrate the invention without limiting it in any way.

EXAMPLE 1

Surfactants

A1) $C_{12/14}$ Coconut oil alkyl oligoglucoside
(Plantaren® APG 600, a product of Henkel KGaA, Düsseldorf/FRG)

A2) $C_{8/10}$ alkyl polyglycoside
(Plantaren® APG 225, a product of Henkel KGaA, Düsseldorf/FRG)

B1) Narrow-range $C_{12/14}$ coconut oil fatty alcohol 2.5 EO adduct ex catalysis with calcined hydrotalcite
(Arlypon® F-NRE, a product of Henkel KGaA, Dusseldorf/FRG)

B2) Narrow-range $C_{12/14}$ coconut oil fatty alcohol 3.6 EO sulfate Na salt ex catalysis with calcined hydrotalcite
(Texapon® K14S-NRE, a product of Henkel KGaA, Dusseldorf/FRG)

B3) $C_{12/14}$ Coconut oil fatty acid monoethanolamide sulfate Na salt

B4) $C_{12/14}$ Coconut oil fatty acid monoethanol 5EO sulfate Na salt

B5) $C_{8/18}$ Coconut oil fatty acid monoglyceride sulfate Na salt

B6) $C_{12/14}$ Coconut oil fatty acid monoglyceride 5EO sulfate Na salt

C1) Dodecylbenzene sulfonate Na salt
(Maranail® A55, a product of Henkel KGaA, Dusseldorf/FRG)

C2) $C_{16/18}$ Tallow fatty acid sulfate Na salt
(Sulfopon® T50, a product of Henkel KGaA, Dusseldorf/FRG)

C3) Normal-range $C_{12/14}$ coconut oil fatty alcohol 3.6 EO sulfate Na salt (Texapon® K14S, a product of Henkel KGaA, Dusseldorf/FRG)

C4) Normal-range $C_{12/14}$ coconut oil fatty alcohol 2.5 EO adduct

EXAMPLE 2

Evaluation of Washing Performance (WP)

Washing performance was tested in a launderometer on a dust/sebum soil on polyester/cotton (crease-resistant) at 40° C. The lightening of the washed swatches was evaluated by photometric remission measurement with an Elrepho RFC-3/24 against a barium sulfate standard of which the remission was put at 100%. The results are expressed in % remission (% R).

Liquor: 250 ml
Liquor load: 1 part by weight fabric/30 parts by weight water
Dosage: 10 g/l
Water hardness: 16° d
Determination: average of 3 determinations The results of the washing tests are set forth in Table 1.

EXAMPLE 3

Evaluation of dishwashing performance (DWP)

Dishwashing performance was determined by the saucer test (Fette, Seifen, Anstrichmitt., 74, 163 (1972)). To this end, saucers 14 cm in diameter were each soiled with 2 ml beef tallow (acid value 9–10) and stored for 24 h at room temperature. The saucers were then rinsed at 50° C. with 5 liters tapwater having a hardness of 16° d. The test mixture was used in a dosage of 0.15 g active substance/l. The dishwashing test was terminated when the foam had completely disappeared. The results of the dishwashing tests, expressed as the number of clean saucers, are set out in Table 1.

EXAMPLE 4

Evaluation of foaming power (FP)

Foaming power was evaluated in accordance with DIN 53 902 by the Götte foam generating method. 1% by weight surfactant solutions in water having a hardness of 16° d were used; the temperature was 20° C. The results of the foam tests, expressed as the basic foam volume in ml, are set out in Table 1.

TABLE 1

| | | | Performance tests | | |
|---|---|---|---|---|---|
| | | | WP | | FP |
| Ex. | Surfactant | | Ratio[1] | %-R | DWP | ml |
| 1 | A1 | B1 | 50:50 | 64.0 | — | — |
| 2 | A1 | B1 | 75:25 | 64.8 | — | — |
| 3 | A1 | B2 | 50:50 | 63.5 | 11 | 400 |
| 4 | A1 | B2 | 75:25 | 63.9 | 12 | 450 |
| 5 | A1 | B3 | 75:25 | 63.4 | 10 | 380 |
| 6 | A1 | B4 | 75:25 | 63.7 | 10 | 390 |
| 7 | A1 | B5 | 75:25 | 63.5 | 10 | 370 |
| 8 | A1 | B6 | 75:25 | 63.8 | 10 | 380 |
| 9 | A2 | B1 | 75:25 | 61.8 | — | — |
| 10 | A2 | B2 | 75:25 | 62.5 | 10 | 340 |
| 11 | A2 | B3 | 75:25 | 60.5 | 10 | 310 |
| 12 | A2 | B5 | 75:25 | 60.4 | 10 | 310 |
| C1 | A1 | — | — | 62.9 | 11 | 320 |
| C2 | A2 | — | — | 58.9 | 3 | 290 |
| C3 | B1 | — | — | 59.7 | — | — |
| C4 | B2 | — | — | 60.0 | 9 | 340 |
| C5 | B3 | — | — | 59.6 | 5 | 300 |
| C6 | B5 | — | — | 59.3 | 5 | 300 |
| C7 | A1 | C1 | 75:25 | 61.4 | 11 | 390 |
| C8 | A1 | C2 | 75:25 | 62.0 | 5 | 370 |
| C9 | A1 | C3 | 75:25 | 61.8 | 11 | 390 |
| C10 | A1 | C4 | 75:25 | 62.0 | — | — |

[1]ratio by weight of surfactants used

What is claimed is:

1. An aqueous detergent composition in which the surfactant component thereof consists of (a) an alkyl or alkenyl polyglycoside of the formula I $$R^1O(G)_n \qquad (I)$$

wherein $R^1$ is an alkyl or alkenyl group containing from one to about 30 carbon atoms; G represents a moiety derived from a reducing saccharide containing 5 or 6 atoms; n is a number having an average value from 1 to about 6; and, (b) a narrow-range fatty alcohol ether sulfate, wherein component (a) is present in from about 30 to about 75% by weight based on the solids content of said composition and component (b) is present in from about 10 to about 70% by weight based on the solids content of said composition.

2. The composition of claim 1 wherein said narrow-range fatty alcohol ether sulfate has the formula III $$R^3-O-(CH_2CH_2O)_n-SO_3X \qquad (III)$$

wherein $R^3$ is a linear or branched alkyl or alkenyl radical having from 6 to about 22 carbon atoms, m is a number from 1 to about 10, and X is an alkali metal or alkaline earth metal.

3. The composition of claim 2 wherein the narrow-range fatty alcohol ether sulfate is an adduct of from 2 to 7 mols of ethylene oxide with saturated $C_{12-18}$ coconut oil fatty alcohols in the form of its sodium or potassium salt.

4. The composition of claim 1 wherein component (b) is present in from about 25 to about 60% by weight based on the solids content of said composition.

5. The composition of claim 1 wherein component (b) is present in from about 25 to about 70% by weight, based on the solids content of said composition.

* * * * *